US00PP15376P3

(12) United States Plant Patent
Challet

(10) Patent No.: US PP15,376 P3
(45) Date of Patent: Nov. 30, 2004

(54) ***CHRYSANTHEMUM* PLANT NAMED 'CHAVINGTROIS'**

(50) Latin Name: *Ajania pacifica*
Varietal Denomination: Chavingtrois

(75) Inventor: Jean-Pierre Challet, Nuaillé (FR)

(73) Assignee: Selection New Plant SARL, Le Luc en Provence (FR)

( * ) Notice: Subject to any disclaimer, the term of this patent is extended or adjusted under 35 U.S.C. 154(b) by 96 days.

(21) Appl. No.: 10/342,290

(22) Filed: Jan. 15, 2003

(65) Prior Publication Data

US 2004/0139514 P1 Jul. 15, 2004

(51) Int. Cl.[7] ..... A01H 5/00
(52) U.S. Cl. ..... Plt./263
(58) Field of Search ..... Plt./263, 284

*Primary Examiner*—Anne Marie Grunberg
(74) *Attorney, Agent, or Firm*—Burns, Doane, Swecker & Mathis, L.L.P.

(57) ABSTRACT

A new and distinct Charm *Chrysanthemum* cultivar is provided that is the result of a controlled breeding program. Attractive small daisy-like blossoms are formed in profusion in clusters having light yellow disc florets and one row of light yellow ray florets. The growth habit is short, bushy, very compact and well-branched with short internodes and yields a generally uniform and spherical overall plant. The foliage has a matte finish, is small and dark green, and contrasts well with the yellow blossom coloration. The upper surface of the leaves possesses a margin that is light greyed-green in coloration. The response time is approximately eight weeks. The natural flowering time is late-October. When mature the blossoms emit a generous quantity of yellow/orange pollen. The plant grows well in pots, and possesses no particular susceptibility to insects and diseases.

1 Drawing Sheet

Figure 1:
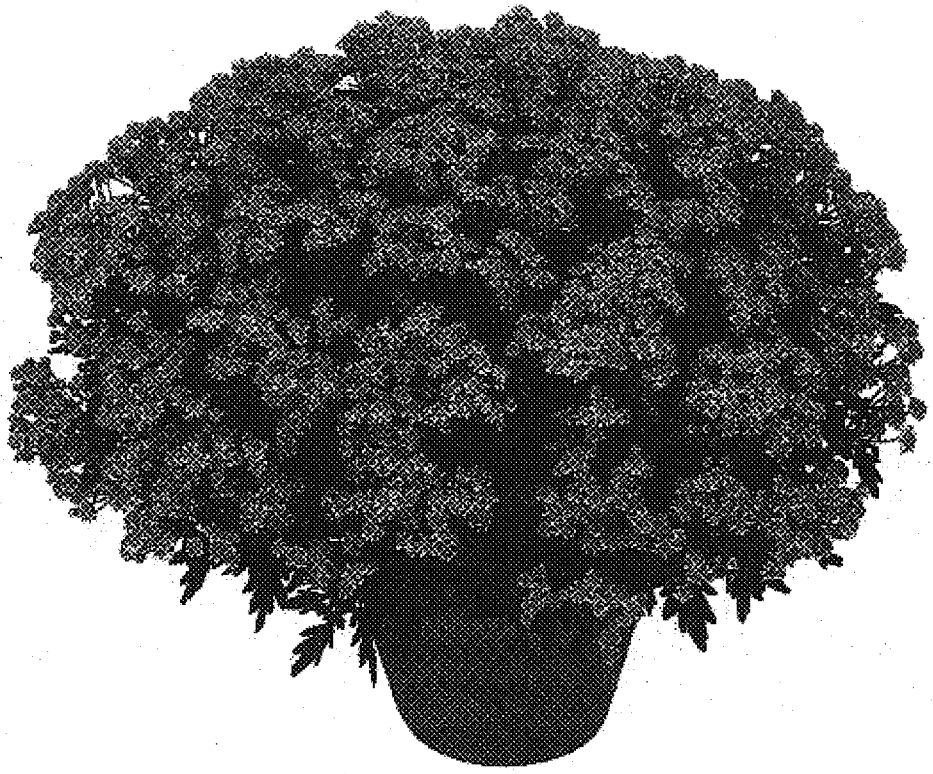

Botanical/commercial classification: *Ajania pacifica*/ Decorative Pot Mum.
Varietal denomination: cv. 'Chavingtrois'.

SUMMARY OF THE INVENTION

The present invention comprises a new and distinct cultivar of *Chrysanthemum*, botanically known as *Ajania pacifica*, and hereafter is referred to by the cultivar name 'Chavingtrois'.

The new cultivar of the present invention was created at Nuaillé, France during the course of a controlled breeding program. The seed parent (i.e., the female parent) was an unnamed plant of the species, and the pollen parent (i.e., the male parent) was designated '94/13/9'. Neither parent was patented in the United States. The seeds resulting from the cross were sown and small plants were obtained which were physically and biologically different from each other. Selective study resulted in the identification of a single plant of the new cultivar of the present invention.

It was found that the new Charm *Chrysanthemum* cultivar of the present invention displays:

(a) a short, bushy, compact, well-branched, and generally spherical growth habit with short internodes, (b) profusely forms attractive small daisy-like blossoms having light yellow disc florets and one row of light yellow ray florets, (c) forms attractive small dark green foliage having a matte finish with a light greyed-green margin on the upper leaf surface, (d) forms a generous quantity of yellow/orange pollen when the blossoms are mature, and (e) an ability to grow well in pots.

The new cultivar can be grown singly or in clumps in pots. It also can be grown in the landscape. The yellow blossoms contrast nicely with the dark green foliage. The plant is self-branching and the internodes are short. Pinching is helpful to further enhance branching and produces a large number of shoots; however, such pinching is not necessary since the plant already is inherently well branched. The natural flowering time is late-October.

The new cultivar can be readily distinguished from its parental plants. More specifically, the female parent displays darker yellow ray florets, a less bushy growth habit, and is natural flowering approximately three weeks later than the new cultivar. The '94/13/9' male parent forms dissimilar orange-yellow flowers, and more typical foliage that lacks a light greyed-green margin on the upper leaf surface that is processed by the new cultivar. No other closely related cultivar is known to Applicant.

Asexual reproduction of the new cultivar by the use of cuttings as performed at Nuaillé, France, in a controlled environment has demonstrated that the characteristics of the new cultivar are firmly fixed and are retained through successive generations of asexual propagation.

'Chavingtrois' has not been observed under all possible environmental conditions to date. Accordingly, it is possible that the phenotype may vary somewhat with variations in the environment, such as temperature, light, day length, contact with pesticides and/or subjection to grown regulation treatments.

BRIEF DESCRIPTION OF THE PHOTOGRAPH

The accompanying FIG. 1 depicts a typical eighteen week-old plant of 'Chavingtrois' cultivar while growing in a pot in a greenhouse at Nuaillé, France. The attractive compact spherical growth habit, with a substantially homogenous coverage of yellow blossoms, and dark green foliage with a light green margin on the upper leaf surface are illustrated.

DETAILED DESCRIPTION

The plants described were grown in pots in a greenhouse at Nuaillé, France. No growth regulation was used. The growing conditions approximate those commonly utilized for the commercial production of decorative pot mums.

Color references are made to tone Royal Horticultural Society Colour Chart (R.H.S.), except where general colors of ordinary significance are used.

General appearance: Short, bushy, and compact with a generally spherical growth habit. The internodes are short and commonly measure approximately 10 to 25 mm on average. When a cutting is placed during week 23 in a four-liter pot, the resulting plant commonly will display a height of approximately 24 to 26 cm on average and a width of approximately 30 to 45 cm on average at the end of flowering during late October.

Foliage: The leaves are elongated and approximately 6 to 8 cm in length on average. Each leaf possesses rough serration and consists of five lobes. The lobes generally possess acuminate tips, the inferior lobe is long, and sinus between lobes generally is rounded. The upper leaf surface is dark green (near Green Group 139A) and bears a light-colored margin of near Greyed-Green Group 191A as illustrated in FIG. 1. The under leaf surface also is near Greyed-Green Group 191A in coloration. The nervure coloration is near Green Group 139A on the upper surface and near Greyed-Green Group 191A on the under surface. The stem is near Greyed-Brown Group 199A in coloration, and the petiole is near Greyed-Green Group 191A in coloration.

Flowers: The attractive small daisy-like blossoms are formed in clusters. The buds possess a smooth surface texture, commonly are approximately 0.4 to 0.5 cm in length on average and are near Greyed-Green Group 191A in coloration with a whitish cast. The flower coverage is substantially homogeneous across the plant. Accordingly, the flowers are so closely grouped as to substantially cover the circumference of the dome-shaped plant. The flowers possess no fragrance. The disc florets are light yellow and are surrounded by one row of light yellow ray florets at maturity. The overall blossom coloration commonly is between Yellow Group 13C and 13D. The number of petals per flower commonly approaches 20 and the petals commonly measure approximately 0.5 to 0.6 cm on average. The flower diameter when mature commonly ranges from approximately 10 to 15 mm. The stigma is near Yellow-Orange Group 15A in coloration. The styles, filaments and anthers are so small and slim that it is not possible to determine their coloration and to provide additional characterization using standard evaluation techniques. A generous quantity of pollen commonly is displayed in the mature blossoms that is near Yellow-Orange Group 15A in coloration.

Flower time: The natural flowering time is late-October. The flowers commonly last approximately 4 to 6 days on average on the plant and such longevity commonly is influenced by the environmental conditions that are encountered.

Response time: The time between the beginning of the short day period and the flowering date at normal temperature and light intensity is approximately eight weeks.

Usage: Decorative pot mum. No particular susceptibility to diseases and pests has been observed during the growing of the new cultivar to date.

What is claimed is:

1. A new and distinct cultivar of Charm *Chrysanthemum* plant that displays:

(a) a short, bushy, compact, well-branched, and generally spherical growth habit with short internodes, (b) profusely forms attractive small daisy-like blossoms having light yellow disc florets and one row of light yellow ray florets, (c) forms attractive small dark green leaves having a matte finish with a light greyed-green margin on the upper leaf surface, (d) forms a generous quantity of yellow/orange pollen when the blossoms are mature, and (e) an ability to grow well in pots;

substantially as illustrated and described.

* * * * *